United States Patent [19]

Sie et al.

[11] 4,120,781
[45] Oct. 17, 1978

[54] PROCESS FOR REDUCING THE LEVEL OF RADIOACTIVITY OF A STREAM OF LIGHT HYDROCARBONS

[75] Inventors: Swan T. Sie; Franciscus H. J. Bukkems, both of Amsterdam, Netherlands

[73] Assignee: Shell Oil Company, Houston, Tex.

[21] Appl. No.: 770,726

[22] Filed: Feb. 22, 1977

Related U.S. Application Data

[63] Continuation of Ser. No. 660,532, Feb. 23, 1976, abandoned.

[30] Foreign Application Priority Data

Feb. 21, 1975 [NL] Netherlands .................... 7502072

[51] Int. Cl.² ............................................. C10G 25/00
[52] U.S. Cl. .................................. 28/251 R; 208/253; 55/74; 423/249
[58] Field of Search .............. 208/251 R, 253; 55/66, 55/74; 423/249, 210; 210/38 C

[56] References Cited

U.S. PATENT DOCUMENTS

| 3,240,555 | 3/1966 | Nash | 423/210 |
|---|---|---|---|
| 3,501,923 | 3/1970 | Lehmer | 55/74 |
| 3,720,043 | 3/1973 | Kovach | 55/74 |
| 3,784,674 | 1/1974 | Stein | 423/249 |
| 3,806,583 | 4/1974 | Dewell | 423/210 |
| 3,940,471 | 2/1976 | Favre | 423/249 |

*Primary Examiner*—Herbert Levine
*Assistant Examiner*—James W. Hellwege

[57] ABSTRACT

The invention relates to a process for reducing the level of radioactivity of a stream of light hydrocarbons by passing the stream through sulfided solid particles.

16 Claims, No Drawings

PROCESS FOR REDUCING THE LEVEL OF RADIOACTIVITY OF A STREAM OF LIGHT HYDROCARBONS

This is a continuation of application Ser. No. 660,532, filed Feb. 23, 1976, now abandoned.

BACKGROUND OF THE INVENTION

It is known that natural gas may contain traces of the radioactive noble gas radon. Radon occurs in the series of products that are formed successively during the natural radioactive decay of uranium. Uranium occurs widely on earth and therefore it may be expected that radon will occur fairly generally in natural gas wherever in the world it is found. The quanity of radioactive material that reaches the earth's surface together with natural gas, however, is only 0.001% of the quantity which the earth produces elsewhere and in widely scattered places.

Radon, being a gas, will easily be entrained by the natural gas. Radon, however, is also subject to decay, yielding particles which are no longer chemically inert and less volatile than radon. It is conceivable that thus radioactive metallo-organic compounds are formed which again are so volatile as to be at least partly entrained with the natural gas. Also, during transport, decay products and compounds thereof will be deposited on walls. Obviously this occurs during the residence and the transport of the natural gas in the earth's crust. Besides, such radioactive products which emerge from a well together with the gas may tend to be deposited on parts of above-ground installations, such as pipelines, drying equipment, separators, valves, etc., which creates a potential danger of an accumulation or radioactive material in places accessible to man. Thus, it has been found that the condensate of light hydrocarbons higher than methane, recovered from the natural gas in a certain field, has a concentration of the radioactive isotope polonium 210 that is measurable through its radiation. This isotope is an alpha radiator with a half life of 138 days. This concentration, however, is very low. The activity concentration is of the order of magnitude of 2 pCi/gram (pivo Curie), which corresponds with a concentration of Po 210 of $10^{-15}$ gat/l. Chemical analysis is impossible because of this very low concentration, and the radiation level is far below the dose that is dangerous to man. Nevertheless, it is highly desirable to reduce the level of radioactivity in order to preclude any hazards due to accumulation on parts of above-ground installations, and the invention provides a process for this purpose.

The invention therefore relates to a process for reducing the level of radioactivity of a stream of light hydrocarbons by passing that stream through a space containing solid particles for the removal of radioactive metals or compounds thereof, which solid particles contain one or more metals from Group VI B, alone or combined with one or more metals from Group VIII B of the Periodic Table, in the sulfidic form, the stream of hydrocarbons being passed through at a temperature lower than 100° C. at a space velocity of 0.1 to 100 kg per hour per liter of space filled with solid particles.

This process can be carried out both with gaseous and with liquid hydrocarbons. The pressure may be chosen freely. In the case of a liquid stream, such as a condensate of light hydrocarbons, a pressure of 1 bar is very suitable because of the relatively cheap apparatus that is required for it.

The surprising feature of the process according to the invention is that when the said sulfided metal-containing particles are used the temperature may be kept below 100° C., while the space velovity may be varied between wide limits. It is not possible to find out exactly what happens during this process, because the initial concentration of the particles to be removed is so low. Even the quantities accumulated on the contact material are still too small for chemical analysis. The measurement of radiation is virtually the only source of information about the particles. It has been found, for example, that the level of radioactivity of condensate originating from a source of natural gas can be reduced 100 to 150 times by a process according to the invention. The possibility that has now been found of working at the very low temperature of less than 100° C., in particular at ambient temperature, is very important in practice, because facilities for maintaining the desired temperature can be omitted. This is especially important with a view to applying the process away from a normal plant, such as on production fields, on artificial islands or in coastal areas where pipelines come ashore.

Sulfidation of the metals may be effected by exposure to a stream of pure $H_2S$ at ambient temperature and 1 bar for 72 hours, followed by stripping with an inert gas such as nitrogen. Sulfidation may also be carried out with an $H_2S/H_2$ mixture, for instance in a molar ratio of 1/7. The temperature may then be increased to 375° C. in 3 hours' time and be maintained at this temperature for another hour. The pressure may be 10 bar. Cooling is effected under $H_2$ at 10 bar. If the stream of hydrocarbons contains any sulfur compounds, sulfidation can be done in situ. If mercaptans are present, it can take place at ambient temperature.

The metals are preferably chosen from the group Ni, Co, Mo and W.

Solid particles containing sulfided metals chosen from the above-mentioned groups are well-known catalysts for various conversions or treatments of hydrocarbons such as hydrogenation and desulfurization of oil fractions. The said metals are then, as a rule, supported on carrier material, mostly inorganic oxides such as $Al_2O_3$ or MgO. For a high catalytic activity the material should have a large internal surface area, for instance, of 150–350 m$^2$/g for catalysts with $Al_2O_3$ as the carrier which means that the material has a microporous structure (average pore diameter smaller than 20 nm). The process according to the invention, when carried out with solids having such structures, has shown to give good results at ambient temperature.

Even better results are obtained when the metals chosen are supported on macroporous carrier material. Better results are also obtained when the carrier material is apolar. Both measures have a similar effect. For, it has been found that solids having a microporous structure will show a decline in activity relatively soon, a tendency which materials that are macroporous and/or apolar show only after very prolonged operation. Although this is not certain, the explanation may be that in a microporous and/or polar solid the active sulfided metals are shielded by water and/or by polar organic compounds usually present in the stream of light hydrocarbons, possibly in traces. The polar inorganic and organic materials may accumulate in the pores by adsorption and/or capillary condensation. Apolar carriers absorb only little or not at all. Materials with a macrostructure have very wide pores that cannot, or hardly, be blocked by adsorbed polar molecules. Materials with a miacroporous structure have a far lower internal surface area than of those with a microporous structure. A boundary line between the two structures is, of course, an arbitrary one, but an indication may be that the internal surface area of macroporous materials is smaller than 100 m²/g and the average pore diameter larger than 30 nm. Experimental resuls show that the process according to the invention does not call for a large internal surface area, which is plausible in view of the very low initial concentration of about $10^{-15}$ gat of radioactive material. Suitable carrier materials are macroporous activated carbon, macroporous silica gel or diatomaceous earth.

An important, advantageous possibility is the use of solid particles consisting entirely of the metals chosen in the sulfidic form, not supported on carrier material. A suitable composition is, for instance, one with Ni, W and S in atomic ratios within the ranges of 0.01-3-Ni:1W:1-4S, for instance 0.5Ni:2S.

This material without a carrier usually has a small internal surface area, less than 100 m²/g, and it is macroporous. The material has a large capacity for reducing the level of radioactivity and does not show any sign of a decline after about 1 months' operation.

Solid particles, in particular those of a microporous and/or polar character, can be regenerated by drying. This can be done by passing a gas, e.g., $N_2$, over the particles at a temperature of 40°-150° C.

A suitable means of counteracting a decline of the capacity for reducing the level of radioactivity, or at least of delaying it, is previous drying of the stream of light hydrocarbons. To this end any conventional drying agent may be used, such as $CaCl_2$, microporous silica gel, etc. The importance of the two above-mentioned measure — regeneration and drying of the incoming stream — decreases according as the solid particles are less prone to a decline in absorption capacity due to the aforementioned causes. As stated before, no distinct boundary line can be drawn. For instance, the water content of the stream of hydrocarbons will also play a part.

The process according to the invention may be carried out under hydrogen pressure. However, the advantages obtained are marginal.

The invention will now be elucidated with the aid of a number of experiments.

For these experiments a stream of light hydrocarbons was used with the following properties:

| paraffins content | 61.5 %w |
| naphthenes content | 17.5 %w |
| aromatics content | 21.0 %w |
| sulfur content | 0.11 %w |
| boiling range | 40-280° C |

EXPERIMENT I

A tube 22 cm long and 2 cm in diameter contained 8 ml solid particles in the form of extrudate 1.6 mm in diameter. The solid particles consisted of $Al_2O_3$ impregnated with sulfided Ni and Mo. The particles contained 2.7 %w Ni and 12.2 %w Mo. The internal surface area was 168 m²/g and the pore volume 0.43 ml/g. The above-mentioned quantity of 8 ml particles had been mixed with 8 ml SiC granules 0.2 mm in diameter, which particles do not reduce the level of radioactivity. This admixture serves to prevent maldistribution of the liquid when being passed thorugh the tube.

A liquid of the above-mentioned composition was passed through at a space velocity of 5 l per 1 solid material/hour at 25° C. and 1 bar. The level of radioactivity of the liquid introduced was 1.29 pCi/g. After it had been passed through, the activity of the liquid was 0.01 pCi/g and this value was still the same at the end of the 24-hour experiment.

EXPERIMENT II

With fresh batches of the same materials and under the same conditions as described under experiment I an experiment of a longer duration was carried out. The space velocity varied somewhat.

The following results were obtained:

| space velocity 1/1/h | liquid passed through, l/1 solid material | activity after passage, pCi/g |
| --- | --- | --- |
| 4.7 | 21 | 0.03 |
| 5.3 | 123 | 0.01 |
| 5.9 | 545 | 0.02 |
| 5.9 | 825 | 0.03 |
| 5.7 | 1244 | 0.04 |
| 5.8 | 1523 | 0.06 |
| 6.0 | 1808 | 0.09 |
| 5.8 | 2225 | 0.09 |
| 6.0 | 2645 | 0.14 |
| 6.2 | 3516 | 0.20 |

The duration of this experiment was 25 days.

It is found that the level of activity of the treated liquid, which is very low in the beginning, is slowly rising, although the level reached after 25 days is still quite acceptable. After these 25 days the solid material in the tube was treated with nitrogen for 18 hours at 40° C. After passing through another 144 l liquid/1 solid material at 25° C. a level of activity of 0.09 pCi/g was measured and after 600 1/1 0.22 pCi/g. So, passing through nitrogen largely restored the absorption capacity of the solid material, which has a microporous structure in this case.

EXPERIMENT III

In order to have a blank experiment, a liquid having an activity of 1.0 pCi/g was passed through solid particles now consisting of non-sulfided Ni-Mo on $Al_2O_3$ in otherwise the same composition and also mixed with SiC particles. During passing through 731 l liquid per 1 solid material to decrease in radioactivity of the liquid was measured.

EXPERIMENT IV

The above-described experiment I was continued, now at a hydrogen pressure of 35 bar at a space velocity of $H_2$ of 200 Nl $H_2$ per 1 liquid. During passing through for 24 hours the level of radioactivity of the treated liquid remained 0.01 pCi/g.

EXPERIMENT V

A tube as mentioned under experiment I was filled with solid particles consisting of Ni and W in the sulfided form, without carrier material. The composition corresponded approximately with the atomic ratio 0.5Ni:1W:2S.

These solid particles had a cross-section of about 1 mm and had not been mixed with SiC particles. The temperature was 48° C.

The following results were obtained:

| space velocity 1/1/h | liquid passed through 1/1 solid material | activity after passage, pCi/g |
|---|---|---|
| 4.6 | 88 | 0.05 |
| 3.6 | 365 | 0.01 |
| 3.6 | 506 | 0.01 |
| 3.0 | 1663 | 0.01 |
| 5.0 | 2231 | 0.01 |
| 4.8 | 3242 | 0.02 |
| 5.0 | 3782 | 0.02 |

After 365 l liquid per l solid material had been passed through a change-over was made to a liquid having a level of activity of 2.6 pCi/g instead of 1.29 pCi/g.

This experiment shows that after passing through a liquid for a considerable time — the length of time is of the same order of magnitude as in experiment II — the radioactivity of the treated liquid has not increased. The material of the solid particles is macroporous.

We claim as our invention:

1. A process for reducing the level of radioactivity of a stream of light hydrocarbons comprising, passing a stream of light hydrocarbons containing radioactive metals or compounds thereof through a space containing solid particles containing, in sulfidic form, one or more metals from Group VI B, alone, or combined with one or more metals from Group VIII B of the Periodic Table, the stream of hydrocarbons being passed through at a temperature lower than 100° C. and at a space velocity of 0.1–110 kg per hour per liter of space filled with solid particles.

2. The process of claim 1 wherein the temperature is ambient temperature.

3. The process of claim 1 in which the solid particles contain a metal selected from the group consisting of Ni, Co, Mo and W.

4. The process of claim 2 in which the solid particles contain a metal selected from the group consisting of Ni, Co, Mo and W.

5. The process of claim 3 in which the metal chosen is supported on macroporous carrier material.

6. The process of claim 3 in which the metal chosen is supported on apolar carrier material.

7. The process of claim 5 in which the carrier material consists of activated carbon.

8. The process of claim 5 in which the carrier material consists of silica gel.

9. The process of claim 5 in which the carrier material consists of diatomaceous earth.

10. The process of claim 1 in which the solid particles consist of Ni, W and S in the atomic ratio 0.01–3Ni:1W:1–4S.

11. The process of claim 1 wherein the stream of light hydrocarbons is a stream of natural gas.

12. The process of claim 1 wherein the stream of light hydrocarbons is a condensate of light hydrocarbons from natural gas.

13. The process of claim 11 in which the solid particles contain a metal from the group consisting of Ni, Co, Mo, and W.

14. The process of claim 13 in which the metal chosen is supported on macroporous carrier material.

15. The process of claim 14 in which the carrier material is $Al_2O_3$.

16. The process of claim 15 in which the $Al_2O_3$ has an internal surface areas of 150–350 $m^2/g$.

* * * * *